United States Patent
Frater et al.

(10) Patent No.: US 8,978,653 B2
(45) Date of Patent: Mar. 17, 2015

(54) MASK WITH GUSSET

(75) Inventors: Robert H. Frater, Lindfield (AU); Joanne Drew, Balgowlah Heights (AU); Michael K. Gunaratnam, Marsfield (AU)

(73) Assignee: ResMed Limited, Bella Vista (AU)

( * ) Notice: Subject to any disclaimer, the term of this patent is extended or adjusted under 35 U.S.C. 154(b) by 1115 days.

(21) Appl. No.: 11/430,051

(22) Filed: May 9, 2006

(65) Prior Publication Data

US 2006/0213520 A1 Sep. 28, 2006

Related U.S. Application Data

(60) Continuation of application No. 10/759,176, filed on Jan. 20, 2004, now Pat. No. 7,107,989, which is a division of application No. 10/322,578, filed on Dec. 19, 2002, now Pat. No. 6,772,760, which is a continuation of application No. 09/885,445, filed on Jun. 21, 2001, now Pat. No. 6,986,352.

(60) Provisional application No. 60/213,251, filed on Jun. 22, 2000, provisional application No. 60/219,618, filed on Jul. 21, 2000, provisional application No. 60/293,992, filed on May 30, 2001.

(51) Int. Cl.
*A61M 16/06* (2006.01)

(52) U.S. Cl.
CPC ........... *A61M 16/06* (2013.01); *A61M 16/0611* (2014.02); *A61M 16/0616* (2014.02); *A61M 16/0622* (2014.02); *A61M 16/0633* (2014.02); *A61M 2206/14* (2013.01)
USPC ................ 128/205.25; 128/206.24

(58) Field of Classification Search
CPC .................... A61M 16/06; A61M 2016/0616; A61M 2016/0605; A61M 2016/0611
USPC .............. 128/206.21–207.18, 204.18, 205.25
See application file for complete search history.

(56) References Cited

U.S. PATENT DOCUMENTS

| | | |
|---|---|---|
| 1,710,160 A | 4/1929 | Gibbs |
| 2,130,555 A | 9/1938 | Malcom |
| 2,133,699 A | 10/1938 | Heidbrink |
| 2,428,451 A | 10/1947 | Emerson |
| 2,625,155 A | 1/1953 | Engelder |

(Continued)

FOREIGN PATENT DOCUMENTS

| | | |
|---|---|---|
| DE | 196 03 949 A1 | 8/1997 |
| EP | 303090 A1 * | 2/1989 |

(Continued)

OTHER PUBLICATIONS

Machine Translation of JP11-000397A, provided by the Japanese Patent Office, Jan. 6, 2009, full document.*

(Continued)

*Primary Examiner* — Justine Yu
*Assistant Examiner* — Timothy Stanis
(74) *Attorney, Agent, or Firm* — Nixon & Vanderhye P.C.

(57) ABSTRACT

A mask system for delivering air to a user includes a suspension mechanism to allow relative movement between a face-contacting cushion and a mask shell. The suspension mechanism also provides a predetermined force to the cushion that is a function of mask pressure, displacement of the cushion or both.

43 Claims, 13 Drawing Sheets

(56) References Cited

U.S. PATENT DOCUMENTS

| | | | |
|---|---|---|---|
| 2,706,983 | A | 4/1955 | Matheson et al. |
| 2,881,444 | A * | 4/1959 | Fresh et al. ............... 2/9 |
| 2,931,356 | A | 4/1960 | Schwarz |
| 3,545,436 | A | 12/1970 | Holloway |
| 4,069,516 | A | 1/1978 | Watkins, Jr. |
| 4,402,316 | A | 9/1983 | Gadberry |
| 4,641,645 | A | 2/1987 | Tayebi |
| 4,665,570 | A | 5/1987 | Davis |
| 4,671,267 | A | 6/1987 | Stout |
| 4,782,832 | A | 11/1988 | Trimble et al. |
| 4,905,683 | A | 3/1990 | Cronjaeger |
| 4,907,584 | A | 3/1990 | McGinnis |
| 4,914,957 | A | 4/1990 | Dougherty |
| 4,971,051 | A * | 11/1990 | Toffolon .............. 128/206.26 |
| 5,074,297 | A | 12/1991 | Venegas |
| 5,080,092 | A * | 1/1992 | Tenna ................ 128/201.19 |
| 5,181,506 | A | 1/1993 | Tardiff, Jr. et al. |
| 5,222,478 | A | 6/1993 | Scarberry et al. |
| 5,243,971 | A | 9/1993 | Sullivan et al. |
| 5,299,448 | A | 4/1994 | Maryyanek |
| 5,349,949 | A | 9/1994 | Schegerin |
| 5,355,878 | A | 10/1994 | Griffiths et al. |
| 5,492,116 | A | 2/1996 | Scarberry et al. |
| 5,503,147 | A | 4/1996 | Bertheau |
| 5,540,223 | A | 7/1996 | Starr et al. |
| 5,542,128 | A | 8/1996 | Lomas |
| 5,647,357 | A * | 7/1997 | Barnett et al. .......... 128/206.24 |
| 5,649,532 | A | 7/1997 | Griffiths |
| 5,655,527 | A | 8/1997 | Scarberry et al. |
| 5,657,752 | A | 8/1997 | Landis et al. |
| 5,662,101 | A | 9/1997 | Ogden et al. |
| 5,921,239 | A | 7/1999 | McCall et al. |
| 5,937,445 | A | 8/1999 | Ravo et al. |
| 5,937,851 | A | 8/1999 | Serowski et al. |
| 6,016,804 | A | 1/2000 | Gleason et al. |
| 6,019,101 | A | 2/2000 | Cotner et al. |
| 6,112,746 | A | 9/2000 | Kwok et al. |
| 6,155,253 | A * | 12/2000 | Gamberini .............. 128/201.18 |
| 6,192,886 | B1 | 2/2001 | Rudolph |
| 6,193,914 | B1 | 2/2001 | Harrison |
| 6,213,125 | B1 | 4/2001 | Reese et al. |
| 6,328,031 | B1 | 12/2001 | Tischer et al. |
| 6,340,024 | B1 | 1/2002 | Brookman et al. |
| 6,345,618 | B1 | 2/2002 | Hayek |
| 6,357,441 | B1 | 3/2002 | Kwok et al. |
| 6,371,110 | B1 | 4/2002 | Peterson et al. |
| 6,412,488 | B1 | 7/2002 | Barnett et al. |
| 6,425,395 | B1 | 7/2002 | Brewer et al. |
| 6,467,483 | B1 | 10/2002 | Kopacko et al. |
| 6,644,315 | B2 | 11/2003 | Ziaee |
| 6,772,760 | B2 | 8/2004 | Frater et al. |
| 6,823,869 | B2 | 11/2004 | Raje et al. |
| 6,914,091 | B2 | 7/2005 | Donald et al. |
| 6,986,352 | B2 | 1/2006 | Frater et al. |
| 7,076,822 | B2 | 7/2006 | Pearce |
| 7,093,599 | B2 | 8/2006 | Chen |
| 2004/0144386 | A1 | 7/2004 | Frater et al. |

FOREIGN PATENT DOCUMENTS

| | | | |
|---|---|---|---|
| EP | 0303090 | B1 | 2/1989 |
| EP | 0334555 | A2 | 9/1989 |
| EP | 0 747 078 | A2 | 12/1996 |
| EP | 0853962 | A2 | 7/1998 |
| EP | 1099452 | | 5/2001 |
| JP | 11-397 | | 1/1999 |
| JP | 2002-503374 | | 1/2002 |
| JP | 2003-535657 | | 12/2003 |
| JP | 2005-337371 | | 12/2005 |
| JP | 3802872 | | 7/2006 |
| WO | WO 9803145 | A1 * | 1/1998 |
| WO | WO 98/04310 | | 2/1998 |
| WO | WO 98/48878 | | 11/1998 |
| WO | WO 01/62326 | | 8/2001 |

OTHER PUBLICATIONS

Laurent Brochard, "Pressure Support Ventilation," Chapter 9, Part IV—Conventional Methods of Ventilator Support, pp. 239-257, 1994.

McPherson et al., "Respiratory Therapy Equipment," Chapter 8, Third Edition, Introduction to Ventilators, pp. 230-253, 1985.

Office Action issued in European Appln. No. 01944732.5 (Nov. 27, 2009).

Japanese Office Action dated Dec. 25, 2012 issued in related JP Appl. No. 2011-160766 w/English Translation.

Final Office Action issued in related Japanese Appln. No. 2005-337371 (Jan. 31, 2012).

Reasons for Rejection issued in Japanese Appln. No. 2005-337371 (Feb. 22, 2011) with translation.

Decision of Rejection issued in a corresponding Japanese Appln. No. 2010-214485 with English Translation thereof (Mar. 26, 2013).

Office Action issued in related Japanese Application No. 2010-214485 (Jun. 12, 2012) with English translation thereof.

Notice of Reasons for Rejection issued in a corresponding Japanese Appl. No. 2011-160766, dated Oct. 1, 2013, with English language translation thereof.

* cited by examiner

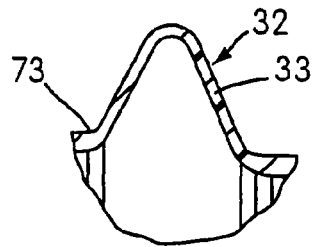
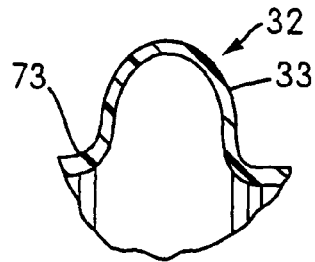
FIG. 6  FIG. 7
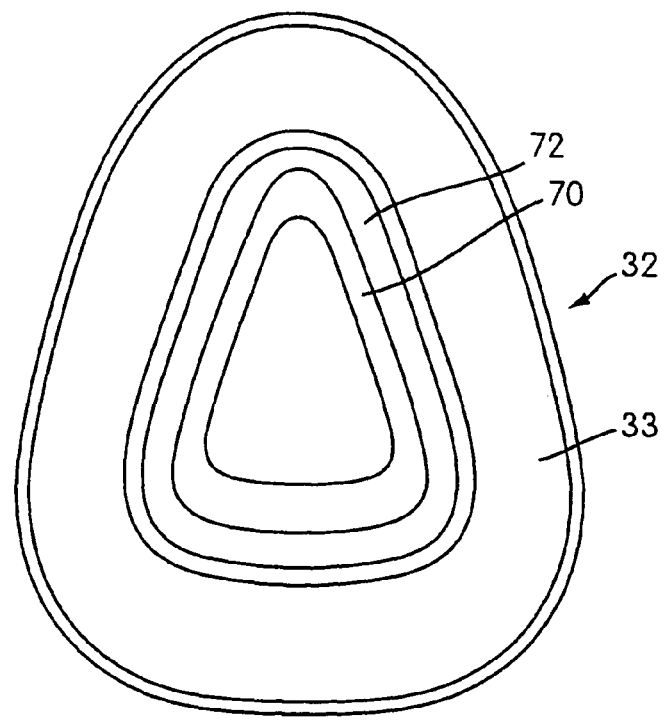
FIG. 8
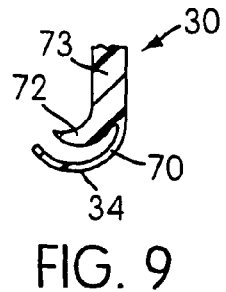
FIG. 9

MASK WITH GUSSET

CROSS REFERENCE TO RELATED APPLICATIONS

This application is a continuation of U.S. application Ser. No. 10/759,176, filed Jan. 20, 2004, now U.S. Pat. No. 7,107,989, which is a divisional of application Ser. No. 10/322,578, filed Dec. 19, 2002, now U.S. Pat. No. 6,772,760, which is a continuation of U.S. application Ser. No. 09/885,445, filed Jun. 21, 2001, now U.S. Pat. No. 6,986,352, which in turn claims the benefit of U.S. Provisional Application No. 60/213,251, filed Jun. 22, 2000, U.S. Provisional Application No. 60/219,618, filed Jul. 21, 2000, and U.S. Provisional Application No. 60/293,992, filed May 30, 2001, each incorporated herein by reference in its entirety.

This invention relates generally to masks for use in respiratory therapy. One use is in CPAP treatment of Obstructive Sleep Apnea. However, the mask arrangements presented herein are useful in other types of respiratory therapy. In the quest for an improved mask arrangement for respiratory therapy, there are various design objectives—effectiveness of seal between the mask and the patient's face, good compliance with a prescribed therapy regime, and patient comfort. The present invention provides various embodiments of a novel mask arrangement, which offers several distinct advantages over known mask arrangements.

BACKGROUND

In respiratory therapy where air is delivered to the mask under pressure, it is important to maintain a good seal between the mask and the patient's face. Leaks between the mask and the patient's face can reduce the desired air pressure in the mask and create increased noise. Both can reduce the effectiveness of, and compliance with, the therapy. In the first instance, the prescribed treatment parameters are not being maintained. In the latter, the increased noise can disrupt the sleep cycle of both the patient and the patient's bed partner.

Leaks are especially prone to occur as the patient moves during the night. Drag and movement of the air delivery tube or the mask system as the patient turns or moves can alter the positioning and alignment of the mask with respect to the patient's face, which movement can be translated or transferred to the cushion seal, creating leaks. Thus, while the mask may initially be leak free when attached to the patient, leaks are prone to develop later in the night as the patient moves in bed, awakening the patient. Hence, patients may tighten straps more than is necessary for pressure requirements in order to reduce or prevent leaks that result from movement.

Many different mask systems are known. One broad group of known mask systems include a rigid shell, a face-contacting cushion and headgear. The shell typically encompasses the nose or nose and mouth. Some known shells encompass the entire face. The cushion is typically constructed from a soft material such as silicone. A headgear provides a means to secure the mask in position. One known form of headgear consists of an arrangement of straps.

Certain mask designs have been developed to increase the flexibility of the mask cushion to enhance patient comfort while maintaining an effective seal between the mask and the patient. The BUBBLE CUSHION® (a registered trademark of ResMed, Ltd.) Mask, covered by U.S. Pat. No. 5,243,971, the subject matter of which is incorporated herein by reference, uses a flexible cushion membrane attached to a mask shell and the pressure inside the mask system to assist in the seal of the cushion membrane itself against the skin or face of the user.

The ResMed MIRAGE® (a registered trademark of ResMed, Ltd.) Mask System, is covered by, inter alia, U.S. Pat. No. 6,112,746, the subject matter of which is incorporated herein by reference, has a contoured, three-dimensionally shaped cushion having an outer face-contacting membrane spaced apart from an inner frame rim to both assist in the seal and increase the comfort of the patient. Neither of these masks incorporates an expanded gusset section for mounting the cushion to the mask to assist in sealing the mask to the patient (user).

A known fitting procedure with a known mask has been to supply the maximum air pressure to the mask that will be supplied to the mask during the therapy and to adjust the strap tension to the necessary level to prevent leaks at that maximum air pressure. However, in many therapy regimens, this maximum air pressure is often encountered only during a portion of the duration of the therapy and the mask air pressure is lower at other times during the therapy. Such is the case, for example, when using auto-titrating or variable pressure systems or during ramp-up when using CPAP systems. Thus, the strap tension is higher than necessary during significant portions of the therapy duration. Further, since leaks are disruptive of both the sleeping cycle and the prescribed therapy regimen, patients will often tighten the straps even more than is necessary to prevent leaks at the maximum encountered air pressure. In known masks, this higher than necessary strap pressure directly results in a higher than necessary force of the mask cushion on the patient's face, particularly as the pressure goes below the maximum mask air pressure.

See FIG. 1, which shows a force diagram for a known mask 110 having a cushion 130 attached to a rigid shell 120. The cushion 130 includes a face-contacting portion 134 attached to a cushion sidewall 173. The cushion sidewall 173 can be relatively flexible, as in the ResMed BUBBLE CUSHION® mask, or relatively rigid, as in the ResMed MIRAGE® mask. Although the mask 110 would be in contact with the face 42 of a patient 40 (shown in phantom) in use, for purposes of clarity in this diagram (as well as the diagram of FIG. 10), a flat foundation 43 is substituted for the patient's face 40. The total force of prior art masks on the user's face $F_m$ has been found empirically to be given by the equation $F_m = F_c + F_{Ac}$, where $F_c$ is the force of the cushion on the patient's face and $F_{Ac}$ is the force on the patient's face of the mask air pressure P inside of the perimeter of $A_c$, the area of contact of the cushion with the patient's face. The force $F_{Ac}$ is given by the equation $F_{Ac} = P A_{Ac}$. Since the force $F_c$ is distributed around $A_c$ and is not merely located at two points on the cushion, as it might seem due to the limitations of the two-dimensional representation of FIG. 1, this force is shown in parentheses. Although $A_c$ is shown inward of the sidewall 173 as would be the case if the mask 110 had just been brought into contact with the user's face with a minimal contacting force, in practice, the face-contacting portion 134 tends to roll under when sufficient force is applied to the mask 110 to seal the mask to the user's face such that $A_c$ can expand outward, toward the sidewall 173.

The force (tension) in the headgear strap $F_s$ for the prior art mask has been found empirically to be given by the equation $F_s = (F_c + F_{Ac})/(2 \cos \theta)$, where $\theta$ is the angle of the head strap with respect to the mask 110. Thus, the force of the cushion on the patient's face $F_c$ is given by the equation $F_c = 2F_s \cos \theta - F_{Ac}$. The force of the mask cushion on the patient's face is difficult to distribute completely evenly around the cushion in known masks, especially at higher forces, and results in localized high pressure spots around the mask cushion. This higher force on the face, and especially the localized high pressure spots, are uncomfortable to the patient and can disrupt the sleep cycle. See, for instance, FIG. 2, which charts the force required to secure a mask on a face versus the air pressure in the mask (measured in centimeters $H_2O$). As seen there, the force required to maintain a known mask sealed to the face throughout a mask air pressure range is most substantially affected by the maximum air pressure in the mask that will occur during therapy. That is, the force of the mask on the face remains at a fairly high level even when the pressure in the mask drops and this force of the mask on the face is directly related to the force necessary to seal the mask at the maximum mask air pressure. Misalignment of the mask will move the curve upward as higher forces are required to seal the mask to the face in light of the misalignment.

This force on the face increases as the head straps of a known mask are tightened to increase the sealing force of the mask, and thereby compressing the cushion and bringing the shell of the mask closer to the patient's face. When the straps are tightened, the shell of the mask moves a distance X between a position $X_0$ when a seal is first obtained to a position $X_p$ when it reaches the point where the cushion is being compressed beyond its normal range. The mask shell may be able to move beyond $X_p$ but the cushion tends to become rigid or nearly so at about $X_p$, thereby limiting further travel. In a known mask, $F_c$ generally increases at a first rate (i.e., the slope of the curve) as the mask moves toward the patient's face within a given range of X. This first rate occurs within the range of flexibility of the face-contacting portion 134. This first rate is also a function of the pressure in the mask acting on a back side of the face-contacting portion 134 of the mask. Thus, as the pressure in the mask increases, the first rate also increases within the given range of X.

However, the known cushion becomes less flexible as it is further compressed beyond such range of X. In a mask having a more flexible sidewall, as discussed above, $F_c$ will then increase at a faster rate as the mask moves toward the patient's face due to a spring-force imparted by the sidewall until such point as the sidewall is nearly completely compressed and directly passing on the force from the rigid mask shell to the face. In a mask having a more rigid sidewall, as discussed above, $F_c$ will then increase at an even faster rate for a short distance as the mask moves toward the patient's face but will quickly reach a point where the rigid sidewall is directly passing on the force from the rigid mask shell to the face.

See FIG. 3, which charts the force required to secure a mask on a face versus the movement of the mask frame (shell) from a relaxed positioned toward the face. The solid curve of FIG. 3 shows the force on the face for a known mask, such as the ResMed Mirage® mask, at a mask air pressure of 10 cms $H_2O$. It can be seen from this curve that the force on the face increases in generally linear proportion to the movement of the mask towards the face within the range of flexibility the cushion 130. However, at such point where the cushion is nearly completely compressed (at approximately 5-7 mm in FIG. 3) so that the generally rigid sidewalls of the cushion 130 begin directly transferring the force from the rigid shell 120 to the face, the force on the face increases dramatically as the mask shell moves toward the face.

U.S. Pat. Nos. 5,492,116 and 5,655,527 to Scarberry disclose a full-face respiratory mask. The mask includes a flexible seal member 18 directly attached to a mask shell 12 and is attached to the user's head by head gear 24. The flexible seal member 18 itself contacts the user's face with a broad area of contact and maintains a seal with the user's face through pressure in the space 62 acting directly upon seal membrane inner surface 54.

Japanese Provisional unexamined patent application (Laid-open Kokai) published Jan. 6, 1999 entitled NASAL MASK FOR RESPIRATION, Provisional Publication No. 11-397 discloses a bellows-formed elastic body between a mask shell and cushion. As seen in the figures of that publication, the bellows portion of the mask projects an area over the patient's face that is substantially the same as the contact area defined by the line of contact of the mask cushion with the patient's face. This publication teaches nothing about the relationship between the area of the bellows and the force applied to the patient's face. Although the bellows provides limited mechanical flexibility, no significant pressure advantages or significant mechanical flexibility can be achieved. This mask does not overcome the sealing problems incurred by movement of the mask with respect to the patient's face without utilizing an increased head strap pressure across the mask air pressure operating range.

SUMMARY OF THE INVENTION

In one aspect, the invention provides a mask system including a shell which in use is positioned in a predetermined position relative to a patient's face, a face-contacting cushion which in use transfers a force to the patient's face, and a means for permitting relative movement between the cushion and the shell wherein said means provides a predetermined force on the cushion. In one form, the predetermined force is a function of mask pressure. In another form, the predetermined force is a function of the displacement of the shell relative to the face. In another form, the predetermined force is a function of both mask pressure and displacement of the shell relative to the face. In another form, the predetermined force is independently controlled. In another form, the means for permitting relative movement between the cushion and the shell is provided by a gusset section positioned in-between the shell and the cushion.

In one aspect, the invention provides a mask system including a face-contacting cushion having a first projected area on the face, a mask shell and a gusset section therebetween, the gusset section having a second projected area on the face wherein the second projected area is greater than the first projected area by greater than approximately 30%.

In another aspect the invention provides a mask system for use at a mask pressure including headgear coupled to a shell which exerts forces on the shell and a face-contacting cushion which transfers forces to the face, constructed and arranged so that the force transferred from the face-contacting cushion to the face is a strong function of mask pressure. The greater projected area of the gusset arrangement with respect to the face contacting area of the cushion uses the air pressure in the mask to expand the gusset into contact with the patient's face, even when the mask shell changes alignment with the patient's face, to provide a more secure seal between the mask and the patient. The expansion, contraction and bending of the gusset allows for enhanced mechanical flexibility over known mask arrangements that helps to maintain a seal even when the patient moves significantly during sleep and the position of the mask with respect to the patient's face changes. Thus, the force of the mask on the face is most significantly proportional to the mask air pressure and the cushion is maintained in secure sealing contact with the patient's face by the mask air pressure over a broader range of positioning of the mask with respect to the patient. This allows for the tension in the straps of the headgear to be generally less than with a known mask to securely seal the mask to the patient's face, especially at mask air pressures below the maximum mask air pressure for the therapy, providing greater patient comfort and compliance with the prescribed respiration therapy regime.

While some membrane-type cushion mask arrangements accommodate limited relative movement between the cushion and the wearer's face while maintaining a tolerable seal, the present invention dramatically increases the level of accommodation without a corresponding increase in the head strap pressure used to secure the mask to the patient. The gusset section provides a flexible component between the mask shell and the cushion in contact with the user's face while reducing the tension required in the headgear to maintain the seal.

Other embodiments of the present invention provide new mask cushion configurations that assist in maintaining the seal between the mask cushion and the user's face.

Another embodiment of the present invention includes the use of a novel baffle element positioned within the interior space of the mask arrangement. The employment of a baffle member within the mask of the present invention minimizes short-circuiting of the intake gas directly to the exhaust vent with the resulting buildup of carbon dioxide. Thus, the baffle serves to reduce the functional dead space of the mask and reduce the level of carbon dioxide rebreathing by the patient.

With the foregoing in mind, other objects, features and advantages of the present invention will become more apparent upon consideration of the following description and the appended claims with reference to the accompanying drawings, all of which form part of this specification, wherein like reference numerals designate corresponding parts in various figures.

BRIEF DESCRIPTION OF THE DRAWINGS

FIGS. 6-7 are partial sectional views of the gusset portion of the mask of FIG. 4 before and after inflation;
FIG. 8 is an end elevational view of a mask shell side of the gusset portion of the mask of FIG. 4;
FIG. 9 is a partial sectional view of the cushion of the mask of FIG. 4.

DETAILED DESCRIPTION OF THE INVENTION

Figure 1:
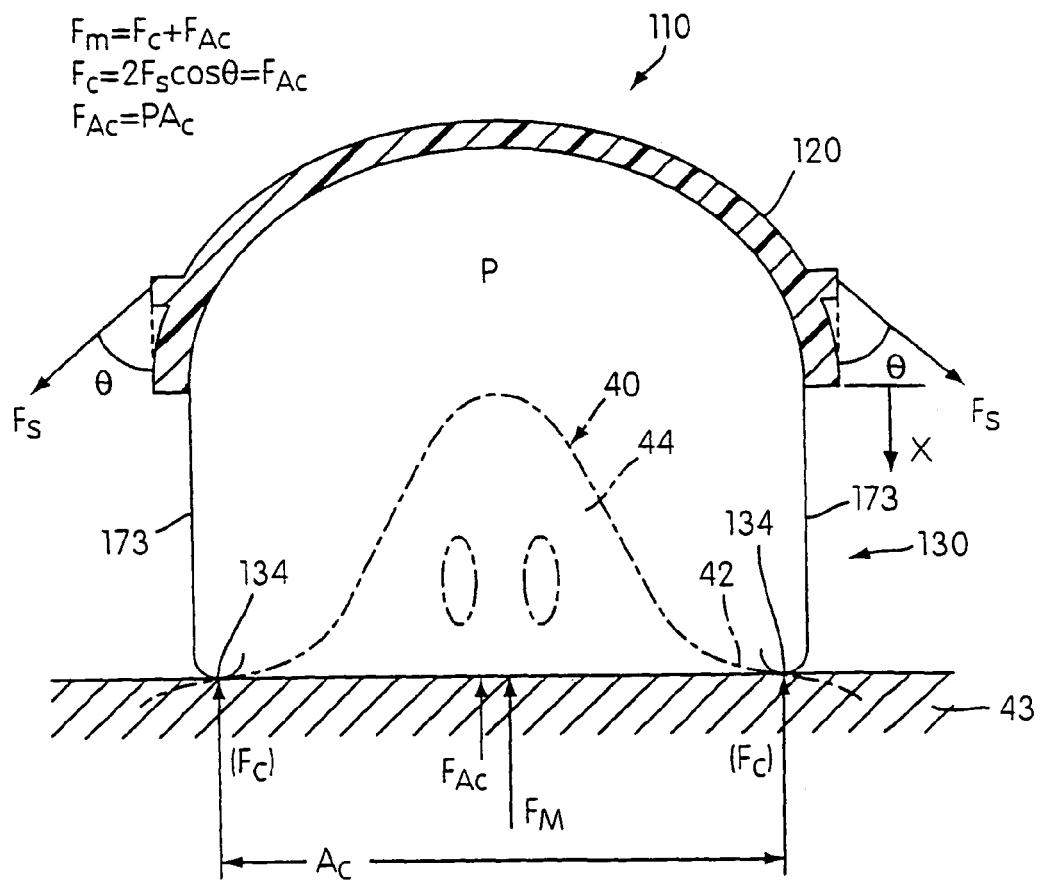
FIG. 1 shows a force diagram for a known mask.
Figure 2:
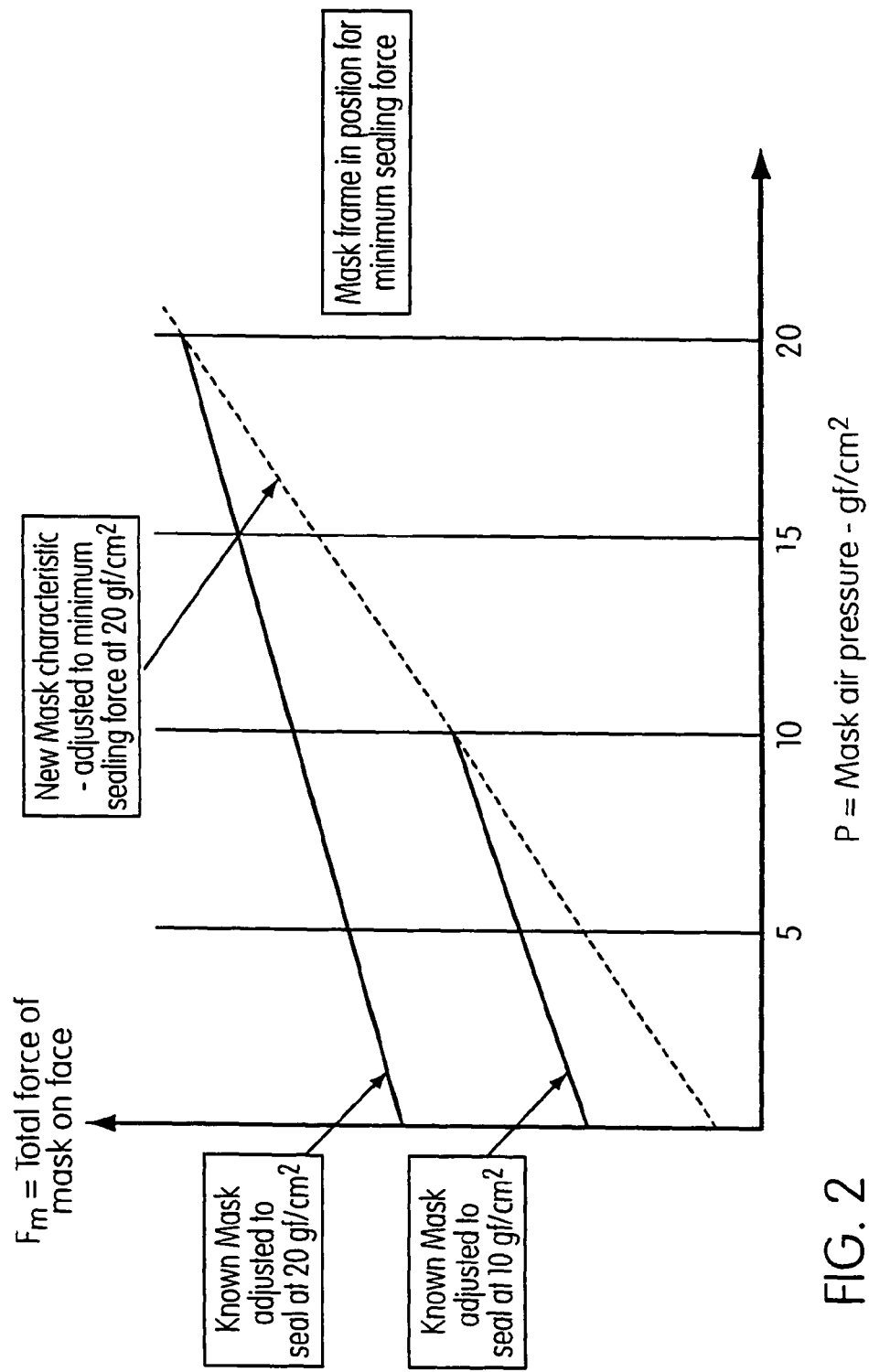
FIG. 2 charts the force required to secure both known and present invention masks on a patient's face versus the air pressure in the mask.

A first embodiment of the respiratory mask 10 of the present invention is shown in FIGS. 4-9. The mask 10 includes a generally rigid shell 20 having an air tube 22 for connecting to a pressurized air supply 25. A gusset portion 32 is attached to the shell 20 in a known manner such as gluing or mechanical fastening. The gusset portion 32 acts as a suspension mechanism for a cushion 30 and includes a flexible gusset sidewall 33. A partial sectional view of the gusset portion 32 is shown in FIG. 6. In this embodiment, the gusset sidewall 33 has a generally uniform thickness and the gusset portion 32 has a generally triangular cross-section when not exposed to mask pressure. However, in this embodiment, the flexible sidewall 33 will balloon out when the mask 10 is pressurized to take on the more rounded cross-section shown in FIG. 7. The FIG. 8 end view of the gusset portion 32 shows that the gusset has a generally triangular outline to conform with the shape of the cushion 30 and shell 20.

Figure 10:
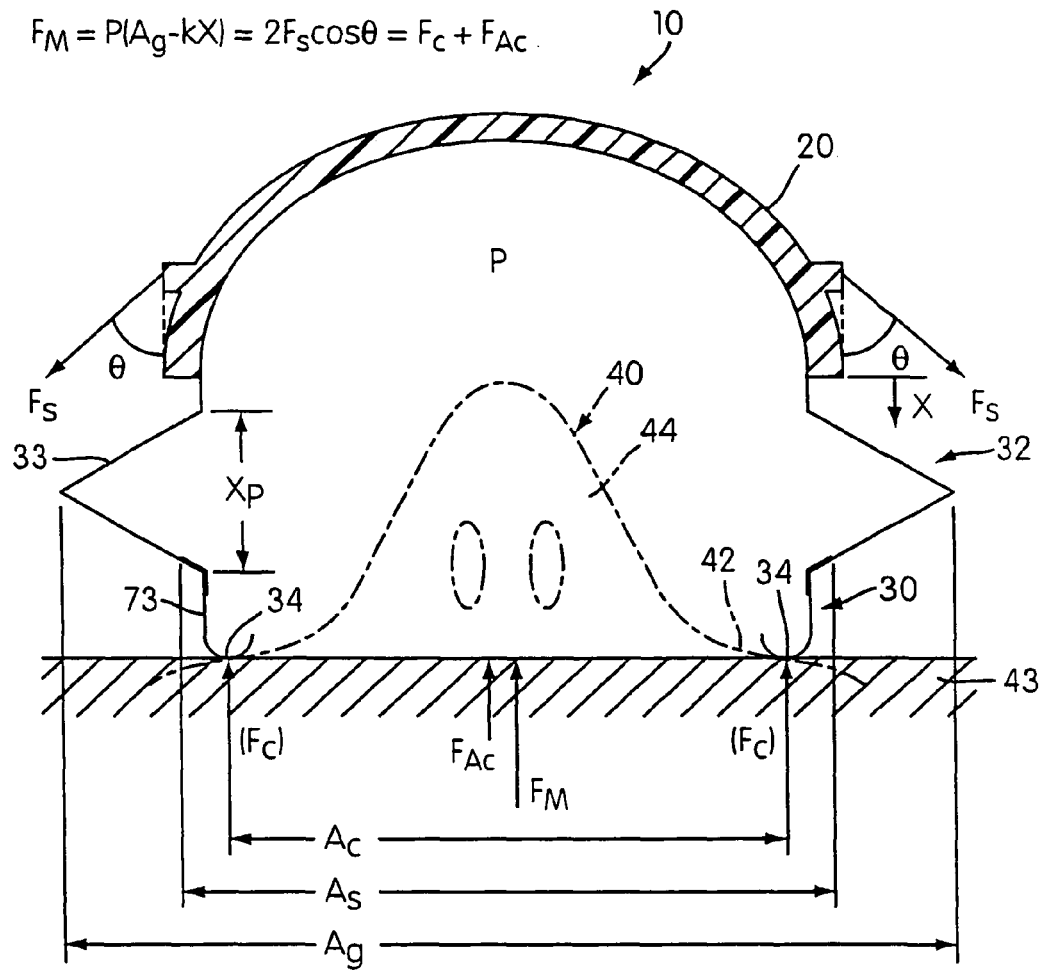
FIG. 10 shows a force diagram of the mask of FIG. 4.

Cushion 30 includes a face-contacting portion 34 that is adapted to engage the face 42 of a patient (user) 40 as shown in FIG. 10. The face-contacting portion 34 of the cushion 30 can be in the form of a standard cushion, such as the ResMed Standard Cushion, or can be in the form of the prior ResMed BUBBLE CUSHION® and MIRAGE® cushions discussed above or in another form as the circumstances warrant. In the preferred embodiment, shown in a partial sectional view in FIG. 9, the cushion 30 of the present invention incorporates an outer membrane 70 that acts as the face contacting portion 34 and an inner rim 72 that provides a backing element for the membrane 70, as does the ResMed MIRAGE® mask. Both the outer membrane 70 and the inner rim 72 are connected to a relatively rigid sidewall 73 that connects with the flexible gusset portion 32. In a worn position, the mask encompasses the naris of the patient and provides a seal around the nose 44. In alternative embodiments, the mask can also enclose both the nose 44 and the mouth of the patient, just the mouth of the patient or the entire face. A headgear 50 (see FIG. 11) having adjustable tensioning straps 52 engages the shell 20 and is used to secure the mask 10 to the patient 40. In the preferred embodiment of the present invention, the headgear and tensioning straps are adjustable as to size but relatively inextensible once adjusted. Mask shell 20 includes an exhaust vent 21 for exhausting gases from the mask and a baffle 23 which will be discussed in further detail below.

Figure 11:
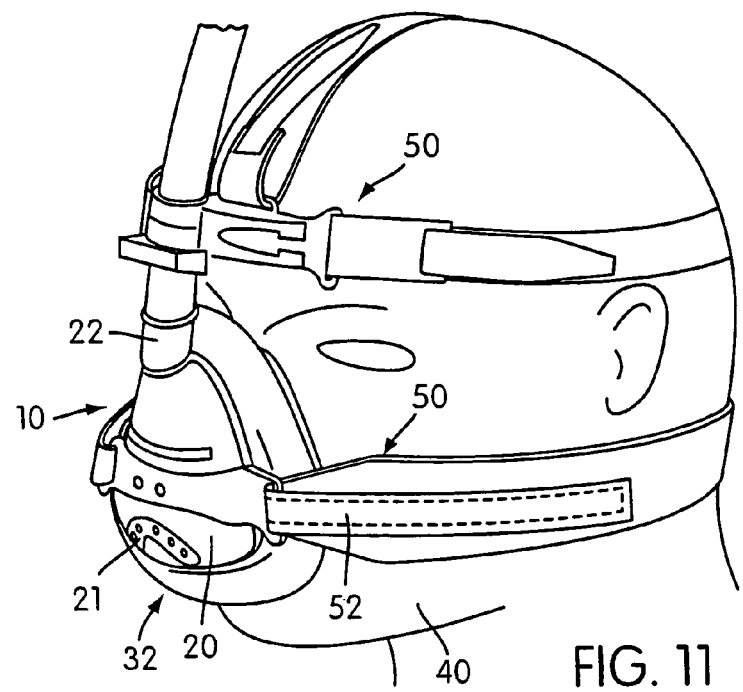
FIG. 11 is a perspective view of a mask of the present invention attached to a patient using strap-based headgear.

The gusset portion 32 includes two key characteristics that provide the benefits of one embodiment of the present invention. The first key characteristic of the gusset portion 32 is that it utilizes the pressure in the mask acting on its increased surface area to provide the primary force for maintaining the face-contacting portion of the cushion in sealing contact with the user's face. The second key characteristic of the gusset portion is that it provides a decoupling joint between the face-contacting portion 34 of the cushion 30 and the mask shell 20, thus allowing some relative movement between the mask and the user's face. This arrangement substantially protects the seal from undue disturbance in the following scenarios: 1) displacement or tilting of mask shell or harness; 2) relaxation of the facial muscles; 3) movement of the patient; and/or 4) movement of the tube. FIG. 11 shows one embodiment of the mask of the present invention attached to a patient.

FIG. 10 shows a force diagram representative of the mask embodiment shown in FIGS. 4-9 (as well as various alternative embodiments of the present invention discussed below). FIG. 10 shows $A_c$, the area of contact of the cushion with the patient's face and $A_g$, the area defined by the gusset portion 32, for the present invention mask.

The area Ag is a projected area on the user's face (i.e., projected on a plane normal to an axis of the mask) of an interior of the gusset portion 32 exposed to the mask air pressure. In the embodiment shown in FIGS. 4-10, Ag extends to the outermost interior surface of the sidewall 33 of the gusset portion 32 and includes Ac. As can be seen, the addition of the gusset portion 32 to the mask 10 results in an area $A_g$ being significantly greater with respect to the area $A_c$ than is found in either the prior ResMed® masks (see FIG. 1) or the mask disclosed in Japanese Provisional Publication No. 11-397, discussed above.

The significance of this can be seen from the following. In one form of the invention, the total force of the mask on the face $F_m$ is given by the empirical equation $F_m=F_c+F_{Ac}=P(A_g-kX)=2F_s \cos \theta$. The force of the cushion on the patient's face $F_c$ is given by the empirical equation $F_c=P(A_g-A_c-kX)$. The force (tension) in the headgear strap $F_s$ is given by the empirical equation $F_s=P(A_g-kX)/(2 \cos \theta)$, where k is the spring constant for the elasticity of the gusset portion and X is the amount of travel of the mask shell toward the face. FIG. 10 also shows $X_p$, the working travel range of the gusset portion 32, although in practice, if the pressure in the mask pushes the face-contacting portion 34 away from the shell 20, $X_p$ can be longer than is shown when the gusset is at rest.

Although k is usually not affected by pressure with respect to a purely mechanical spring, it has been found that within the pressure ranges occurring in the mask of the present invention, that k is proportional to both pressure and distance traveled. Thus, while in the present invention, the maximum force on the face $F_m$ that could be expected to be exerted within $X_p$ would be $PA_g$, testing has shown that this is reduced by the k factor which is both proportional to pressure in the mask and distance traveled.

For a prior art mask configuration, it is seen from FIG. 1 that the force in the headgear strap $F_s=(F_c+PA_c)/(2 \cos \theta)$. For the present invention mask, it is seen from FIG. 10 that the force in the headgear strap $F_s=P(A_g-kX)/(2 \cos \theta)$. The area defined by the gusset $A_g$ is substantively larger than the area in contact with the face $A_c$. Therefore, at the point at which the cushion touches the face (the theoretical initial seal point when both $F_c$ 32 0 and X=0), the force in the straps for the known mask will be $PA_c(2 \cos \theta)$ as opposed to $PA_g/(2 \cos \theta)$ for the present invention mask. However, in reality, a contact force $F_c$ greater than zero is required to: 1) maintain the seal between the face and the cushion because the profiles of the face and cushion are not perfectly matched, and 2) maintain this seal during movement of the face relative to the shell. This force is balanced by the tension in the headgear straps in the known mask system and balanced by the pressure acting upon the gusset area alone, $A_g-A_c$, in the present invention mask system. Thus, within the normal operating mask air pressure range, and especially at lower operating mask air pressures, it has been found that the headgear tension $F_s$ is lower in the present invention mask system.

From FIG. 10, it can also be seen that for the present invention mask, the contact force between the cushion and the face is proportional to the mask pressure, $F_c=P(A_g-A_c-kX)$. This has significant implications in therapies where the mask air pressure varies during either the course of a breath or breath-to-breath or to meet other therapeutic needs. With known mask configurations, where the force of the cushion on the face varies little, if at all, with respect to the pressure in the mask, the tension in the straps must be set sufficiently high at low pressures such that the contact force of the cushion on the face is sufficient to maintain the seal with the face when higher pressures are reached.

For the present invention configuration, both the cushion contact force and the strap tension are significantly affected by the pressure in the mask due to the significantly increased area of the gusset. Therefore, as they both are most proportional to the pressure in the mask, they both will be significantly lower at low pressures and increase as the pressure reaches higher pressures.

In fact, in practice, it has been found that this holds true even at maximum mask air pressures. As an example, assume that $A_c$ is the same in both a known mask (as, for instance, the ResMed MIRAGE®mask) and the inventive mask (both using, say, the same configuration in the face-contacting portion of the cushion). $F_{Ac}$ would be the same in both cases. Then you might expect that given proper alignment of both masks, the minimum necessary $F_c$ for sealing the masks at a given pressure would be the same in both the known and inventive masks and thus, the required $F_m$ to seal at a given pressure to be the same in both cases. However, testing has shown that the present invention mask will seal at a lower force on the cushion, a lower force on the face, and a lower tension in the straps, even at the maximum mask air pressure, than the known mask. It is believed that the test results reflect the real world situation. That is, no face is identical and exactly conforms to the cushion and further, that it is extremely difficult to maintain exact alignment of the mask with the face. This is even more the case with older and/or overweight patient that have loose skin, wrinkles and/or skin folds that hamper the sealing of the mask to the face. Testing has shown that the present invention mask is better able to accommodate these inconsistencies from user to user and provide better sealing performance at lower forces on the face (even at the maximum mask air pressure) than the known mask.

Figure 3:
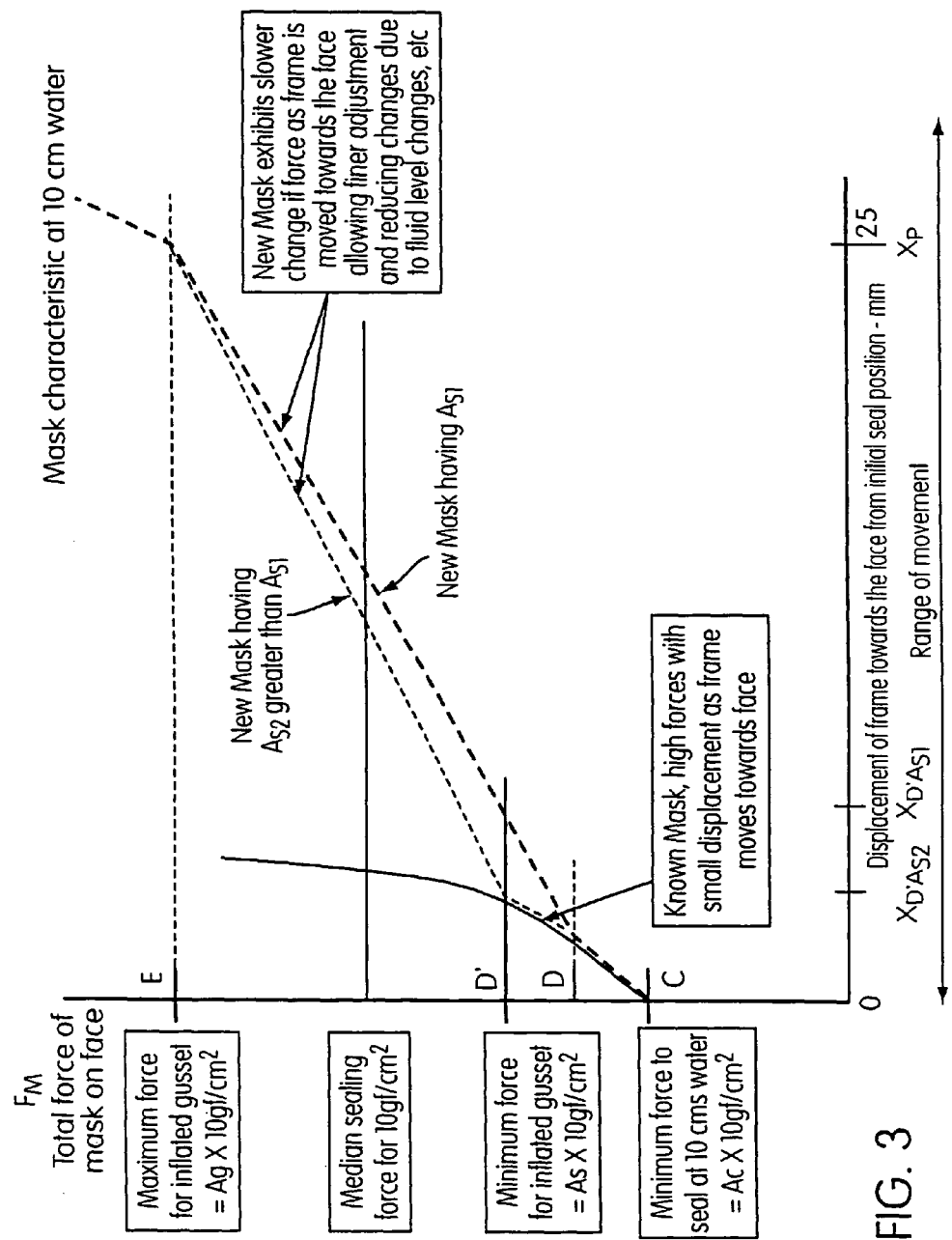
FIG. 3 charts the force required to secure both known and present invention masks on a patient's face versus the movement of the mask shell from a relaxed positioned toward the patient's face.
Figure 4:
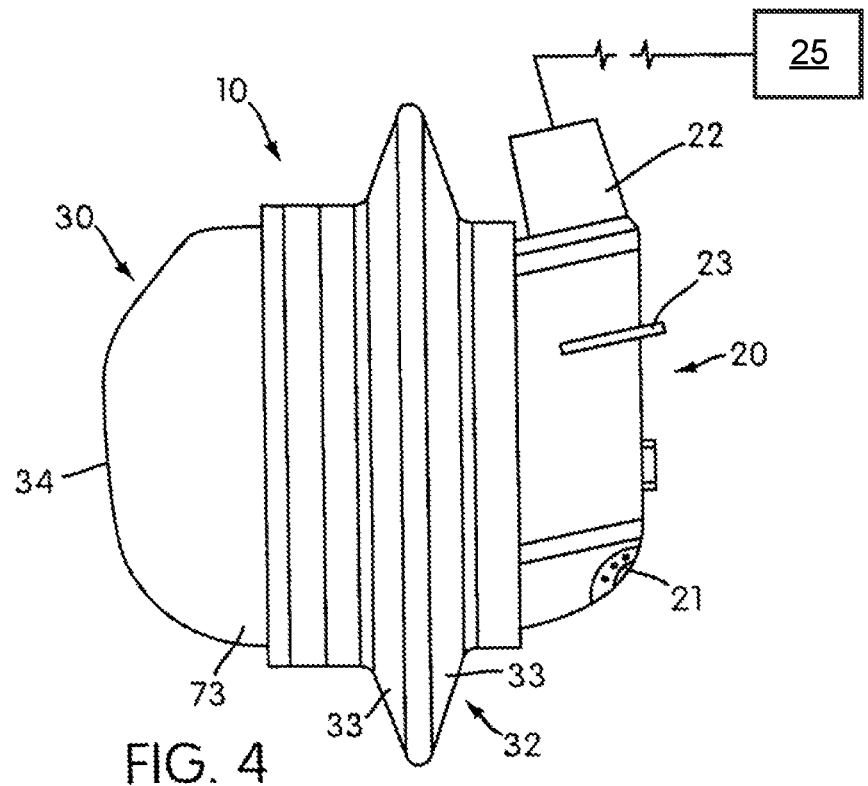
FIG. 4 shows a side elevational view of a mask of the present invention.
Figure 5:
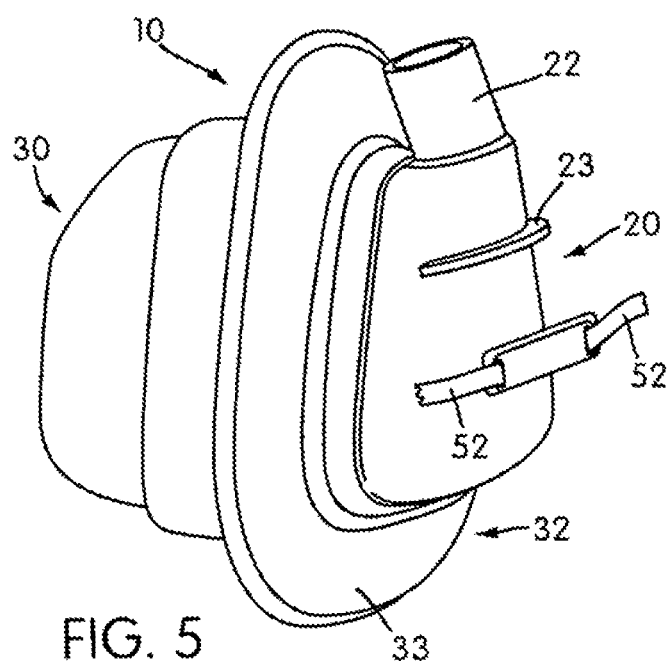
FIG. 5 shows a perspective view of the mask of FIG. 4.

See also the chart in FIG. 3 that shows a comparison of the present invention mask and known masks with respect to the force on the face as the mask shell moves toward the face. As long as the present invention is within the range $X_p$ of the gusset, there is no sharp increase in the force on the face as with the known masks as the mask shell approaches the face. Beyond $X_p$, the force on the face will increase more dramatically, as happens with the known mask, so it is desirable when adjusting the headgear to bring the face contacting portion of the cushion only near or in very light contact with the face. In this way, the gusset is not compressed substantially so that in use the mask is still within the $X_p$ range. This is possible because the seal is maintained by the pressure in the mask and not by compression of the cushion by the headgear. Adjustment of the headgear and mask is thus much simpler than in the known masks. While the range of $X_p$ can be varied for different patients and therapies by varying the size and shape of the gusset section, it has been found that an $X_p$ of between 10-30mm has been effective. It is noted that the curves shown in FIG. 3 are for a mask air pressure of 10 gf/cm² (grams force/centimeter²) These curves can be expected to rise and lower as the mask air pressure is increased and decreased, respectively, but will generally maintain the same shape within the operating pressure range of the mask.

In one embodiment of the present invention shown in FIGS. 4-9, the gusset and cushion are integrally molded of Silastic® 94-595 HC Liquid Silicone Rubber from Dow Corning®, the gusset sidewall 33 has a uniform thickness of 0.5 mm, the gusset has a long length (of the generally triangular $A_g$) of approximately 105 mm and the long length of the generally triangular $A_c$ is approximately 71 mm. The $X_p$ is approximately 25 mm. Thus, the gusset ($A_g$) extends generally beyond the face-contacting portion of the cushion ($A_c$) by approximately 17 mm on each side. This provides for approximate figures for the $A_c$ of 31.5 cm², the $A_g$ of 75 cm², a gusset only area ($A_g$-$A_c$) of 43.5 cm² and an $A_g/A_c$ of approximately 2.4 (or 240%). These dimensions can be altered for different force relationships as desired, but in the preferred embodiments, $A_g/A_c$ will be in the range of about 1.30-5.00 and desirably in the progressively narrowing ranges of 1.50-5.00, 2.00-4.00, and 2.25-3.50, but can be adjusted to fall within any range within the overall range of 1.30-5.00 or even within a range extending beyond that range if circumstances warrant. This compares with an estimated $A_g/A_c$ for the mask example disclosed in Japanese Provisional Publication No. 11-397 discussed above of approximately 1.08.

In the preferred embodiment of the mask, the total force applied to the face $F_m$ is approximately constant at between 35 to 108 grams per gf/cm² mask air pressure, preferably between about 40 to 88 grams per gf/cm² mask air pressure and most preferably between about 50 to 88 grams per gf/cm² mask air pressure. The force applied by the surface area in contact with the face $F_c$ is maintained at an approximately constant proportion to the mask air pressure being delivered to the user and is maintained between about 8 to 61 grams per gf/cm² mask air pressure, preferably between about 27 to 61 gms per gf/cm² mask air pressure and most preferably between about 40 to 61 grams per gf/cm² mask air pressure over a mask air pressure range of 4 to 25 gf/cm². The force $F_c$ is also maintained within a range of about 0.3-4 grams per gf/cm² pressure of the supply of pressurized breathable gas per linear centimeter around a circumference of the cushion in contact with the user's face, preferably within a range of about 0.5-4 grams per gf/cm pressure of the supply of pressurized breathable gas per linear centimeter around a circumference of the cushion in contact with the user's face, more preferably in a range of about 1-3 grams per gf/cm² pressure of the supply of pressurized breathable gas per linear centimeter around a circumference of the cushion in contact with the user's face, and most preferably in a range of about 1.5-3 grams per gf/cm² pressure of the supply of pressurized breathable gas per linear centimeter around a circumference of the cushion in contact with the user's face over a mask air pressure range of 4 to 25 gf/cm². Although the preferred force ranges for the various forces are set forth in this paragraph,-it should be recognized that the force ranges can be set between any two points within the respective overall force ranges given. It is noted that in the industry of the present invention, most pressure measurements are given in centimeters water and that 1 centimeter water=1 gf/cm²=98.07 Pascals.

The gusset portion also allows the mask to maintain a seal with the patient's face over a range of about plus or minus 8° out of alignment with the patient's face.

It has also been found that the shape of the curve for the inventive mask shown in FIG. 3 can be varied by altering the cross-section of the gusset or by providing a backstop for the gusset. Where the gusset has a very uniform thickness and curve, as shown in FIGS. 6 and 7, the curve for total force on the face versus movement of the mask toward the face will be generally linear within $X_p$. It has generally been found desirable in testing to apply a higher sealing force earlier as the mask shell travels toward $X_p$. That is, it is advantageous to move from C, the minimum force to seal at the given pressure, toward D, the minimum force for the inflated gusset, earlier in the travel of the mask shell toward $X_p$. This provides a greater remaining amount of $X_p$ within which the mask will operate and a more gradual increase of the force of the mask on the face as the mask shell moves toward $X_p$ within the remaining amount. The embodiments shown in FIGS. 12-14 help accomplish this goal.

Figure 12:
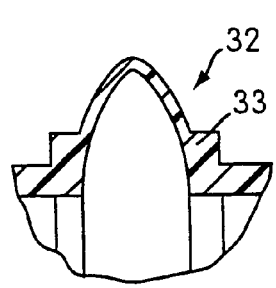
FIG. 12 is a partial sectional view of an alternative embodiment of the gusset portion of the present invention.
Figure 13:
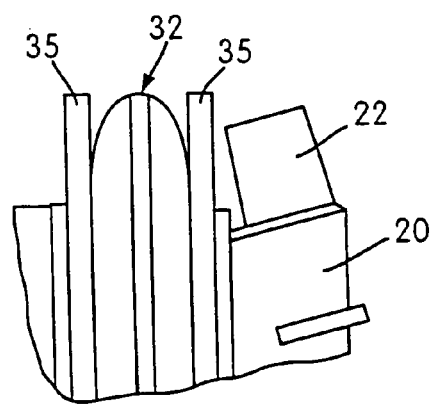
FIG. 13 is a partial side elevational view of an alternative embodiment of the gusset portion of the present invention.

In the first example, shown in FIG. 12, the bases of the gusset sidewall are thickened in an abrupt manner to stiffen the sidewall. In this embodiment, the force-displacement curve for the mask generally follows the curve for the cushion (i.e., the curve for the known mask shown in FIG. 3) as it moves from C toward D and then a lower, generally linear slope until reaching $X_p$. See the long-dashed curve in FIG. 3. However, changing the value for D can alter this curve. The value for D is calculated by multiplying the area for the stiffened portion of the gusset sidewall by the pressure in the mask. The stiffened portion of the gusset sidewall is shown as $A_s$ in FIG. 10. If however, the value of $A_s$ is increased by stiffening a greater portion of the gusset sidewall, the value of D will increase. See the value for D' shown in FIG. 3 and the short-dashed curve that corresponds to a mask embodiment where a greater portion of the gusset sidewall has been thickened (stiffened) to increase $A_s$. Thus, the long-dashed curve represents a gusset embodiment as shown in FIG. 12 having an $A_{s1}$ and the short-dashed curve represents a gusset embodiment as shown in FIG. 12 having an $A_{s2}$ greater than $A_{s1}$. It can be seen from FIG. 3 that the gusset embodiment having the $A_{s2}$ has reached the value D' much sooner as the mask shell moves toward Xp than the gusset embodiment having the $A_{s1}$, thereby leaving a greater remaining amount of the range Xp within which the mask shell can move in use.

Figure 14:
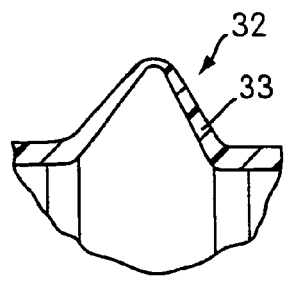
FIG. 14 is a partial sectional view of an alternative embodiment of the gusset portion of the present invention.

A similar effect can be obtained by adding rigid backstops to the embodiment of FIGS. 6 and 7. See FIG. 13, which shows an embodiment where rigid backstops 35 are attached to one or both of the gusset portion 32 and the shell 20. The rigid backstops contact the sidewalls of the gusset in the inflated mode and act as stiffeners to the portions of the sidewall that are contacted. Thus, the rigid backstops can provide the same effect as the embodiment of FIG. 12. The backstops 35 can be placed on one or both sides of the gusset portion and can extend around either a portion, or all, of the perimeter of the gusset portion, as is necessary to provide the desired curve. The backstops can be made of the same material as the mask shell 20 and in one embodiment, one or both backstops 35 can be molded integrally with the shell 20. In alternative embodiments, the configurations shown in FIGS. 6, 7, 12, 14 and 16 can be used in combination with one another, i.e., one configuration on one side of the gusset and another configuration on the other side of the gusset, to specifically tailor the force/travel curve as desired. The thicknesses and dimensions of the various embodiments can also be altered to specifically tailor the force/travel curve. This ability to readily and specifically tailor the force/travel curve of the mask by altering gusset configurations and dimensions is another unique and advantageous aspect of the present invention.

Where the gusset has sidewalls having a tapered thickness, as shown in FIG. 14, the resulting force-displacement curve will lie between the curve for the embodiment of FIG. 6 and the curve for the embodiment of FIG. 12 (assuming comparable gusset base and intermediate thicknesses for the two embodiments).

The gusset portion need not be in the single gusset form discussed above, but can have alternative configurations, examples of which are shown in FIGS. 15-18, along with the $A_c$ and $A_g$ for each example.

Figure 15:
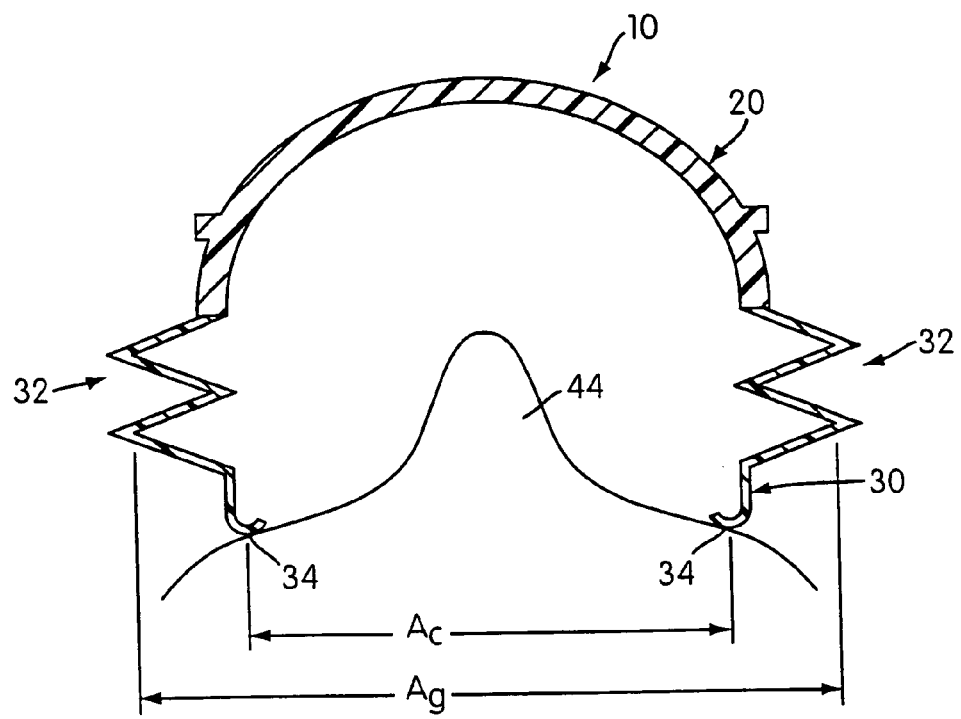
FIGS. 15-18 show sectional views of alternative embodiments of the mask of the present invention in contact with a patient's face.
Figure 16:
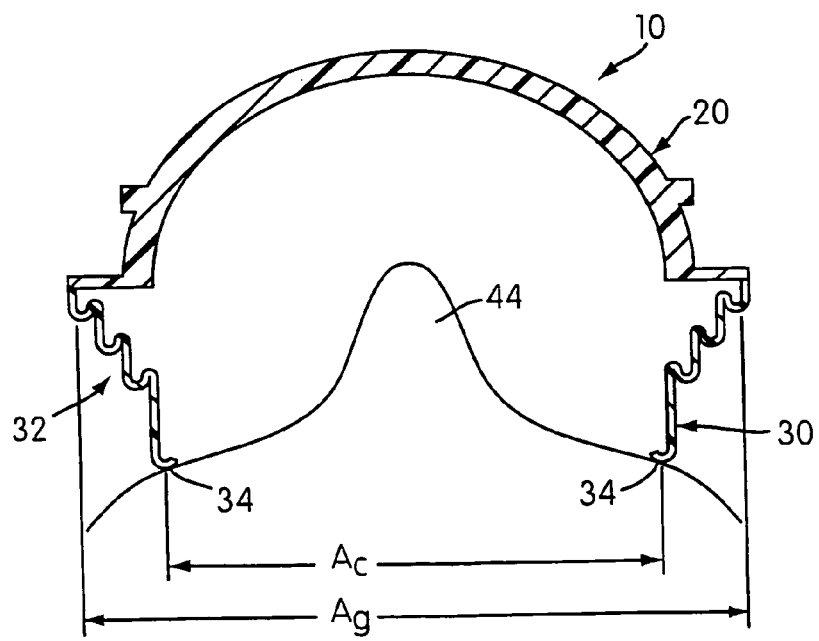
Figure 17:
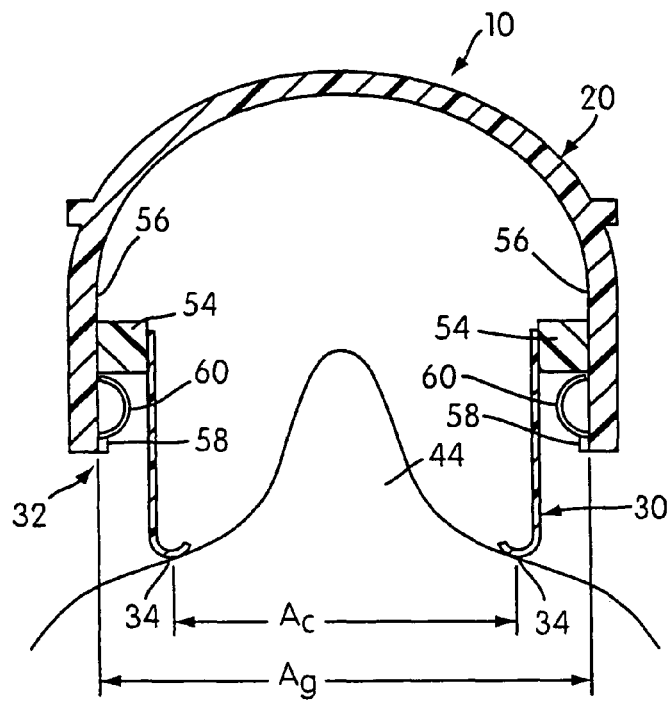

FIG. 15 shows an alternative embodiment of the mask 10 where the gusset portion 32 is in the form of a double gusset providing the decoupling joint between the face-contacting portion 34 of the cushion 30 and the mask shell 20. Of course, three or more gussets can be used in alternative embodiments of the gusset portion 32. FIG. 16 shows an alternative embodiment of the mask 10 where the gusset portion 32 is in stepped form to provide the decoupling joint between the face-contacting portion 34 of the cushion 30 and the mask shell 20. While three steps are shown in FIG. 16, one or more steps can be used in alternative embodiments. One advantage of this embodiment of gusset is the ease in molding the gusset portion 32 and cushion 30 together, since the shell side of the gusset portion 32 is completely open, i.e., there are no hidden surfaces. FIG. 17 shows an alternative embodiment of the mask 10 where the gusset portion 32 is in the form of a piston 54 at the base of the cushion 30 axially slideably engaged with a cylinder portion 56 of the shell 20. The piston 54 can thus move the cushion 30 in and out of the shell 20 to provide a decoupling joint between the face-contacting portion 34 of the cushion 30 and the mask shell 20. A stop 58 can be provided on the shell 20 to prevent the piston and cushion from completely disengaging with the shell 20 under pressure. A spring 60 can optionally be provided to push the piston 54 back into the shell 20 when the air pressure in the mask is decreased. The existence of the spring also simulates the elastic resistance of the gusset portions discussed above and adding a kX factor to the $F_m$ equation. Without the spring, k would equal 0 within the range of movement of the piston.

Figure 18:
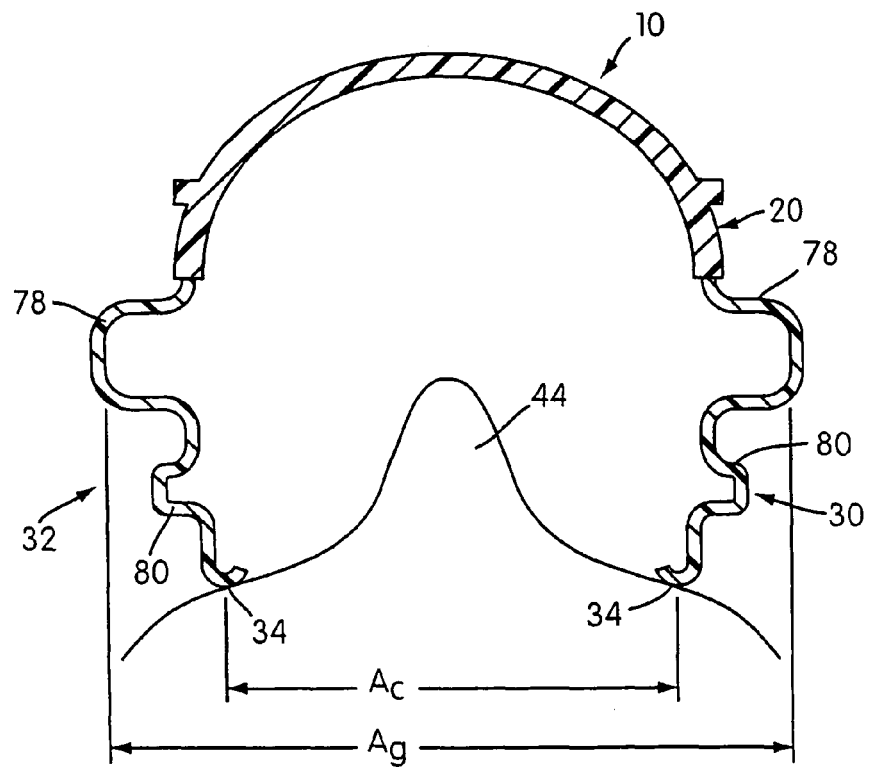

Yet another alternative mask configuration is shown in FIG. 18 which includes a gusset portion 32 having a larger upper barrel shaped gusset 78 and a lower smaller barrel shaped gusset 80. Alternatively, the larger and smaller gussets can be reversed, made the same size or even given different configurations to custom tailor the force characteristics.

Figure 21:
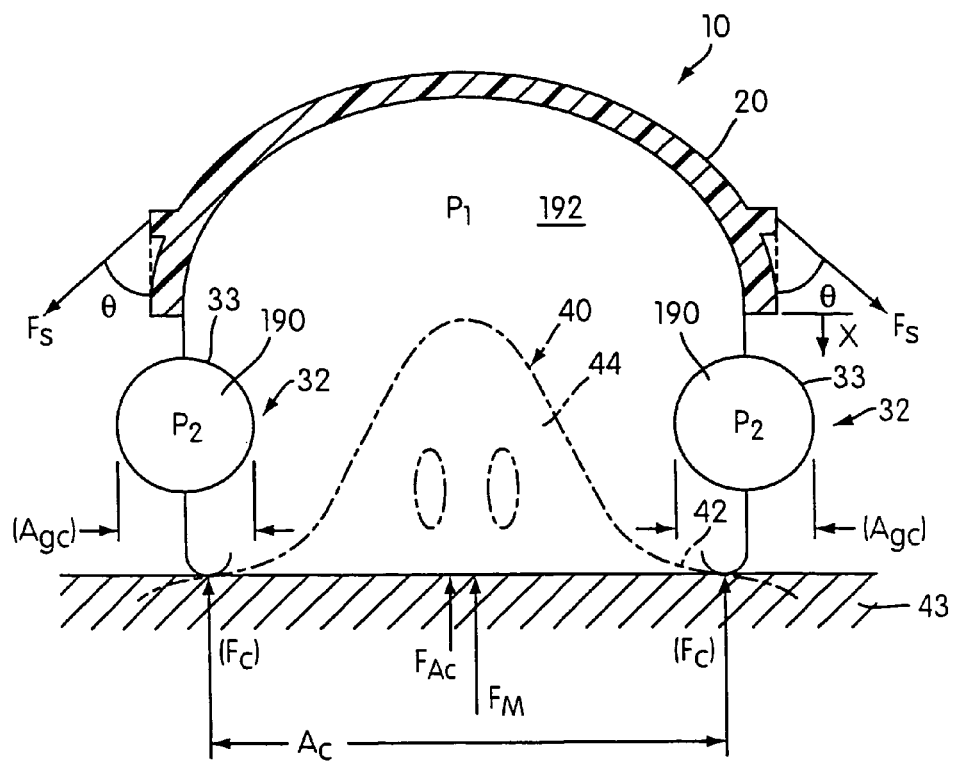
FIG. 21 shows a diagrammatic view of an alternative embodiment of the present invention.
Figure 23:
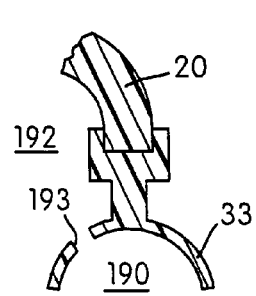
FIG. 23 shows a partial sectional view of one alternative of the embodiment of FIG. 21.

FIG. 21 shows an alternative embodiment of the mask of the present invention wherein the gusset portion 32 has a flexible sidewall 33 having a generally circular or round cross-section enclosing a gusset chamber 190 having an interior volume separated from an interior 192 of the mask shell 20. In one version of this embodiment the gusset chamber 190 can be connected to the mask shell interior 192 through at least one port 193 in the sidewall 33. See FIG. 23. In such a case, a pressure $P_2$ in the gusset chamber will be the same as a pressure $P_1$ in the interior of the mask shell, the effective area of the gusset portion 32 $A_g$ will extend to the outermost interior surface of the gusset sidewall 33, and the gusset portion will operate similarly to the embodiment shown in FIG. 10. However, in a preferred version of this embodiment, the interior of the gusset chamber 190 is connected through a port in the sidewall 33 to a separate pressurized supply of gas than is connected to the mask shell interior so that the pressure $P_2$ in the gusset chamber 190 can be controlled to be at a different pressure than the pressure $P_1$ in the mask shell interior 192. Thus, the force imparted by the gusset portion will be a product of the pressure $P_2$ and the area of the gusset portion. Further, in this embodiment, the area of the gusset portion is no longer determined by the outermost interior surface of the gusset sidewall as in the previous embodiments, but will be the projected area of the entire gusset chamber 190, including the area of the gusset chamber radially inward from the cushion sidewall. This area of the gusset chamber $A_{gc}$ is shown in parentheses in FIG. 21. This provides a high degree of flexibility in controlling the gusset portion and the mask.

First, if additional sealing force is needed from the gusset portion, the pressure $P_2$ can merely be increased, or vice-versa if less sealing force is needed. Second, since the force imparted on the cushion by the gusset portion is a product of the pressure $P_2$ and the area of the gusset portion $A_{gc}$, the area $A_{gc}$ is less critical than in the previous embodiments because it can be offset by changes in the pressure $P_2$. For instance, the outer periphery of the gusset portion can be made smaller in this embodiment than in the previous embodiments because an interior portion of the gusset portion is now also adding to the pressurized area of the gusset portion. Further, the area $A_{gc}$ of the gusset chamber can be varied as desired, and especially made smaller, by varying the pressure $P_2$. This allows the mask to be made smaller, as compared to the other masks discussed above, to be less intrusive and more comfortable to the patient.

The pressure $P_2$ can be controlled to be in relatively constant proportion to $P_1$ or can be controlled to be in varying proportion to $P_1$ as the circumstances warrant. While it is currently believed that in most therapies, $P_2$ will be greater than $P_1$ for most, if not all, of the therapy, it is contemplated that in certain situations, controlling $P_2$ to be less than $P_1$ can be desirable. In some instances, it is contemplated that $P_2$ be held constant. The gusset chamber in this embodiment is intended to be connected only to the second pressurized gas supply and otherwise be closed, especially to the atmosphere. Thus, there should be minimal leakage from the gusset chamber and the second pressurized gas supply need only supply a small volume of gas, significantly less than the volume of gas that must be supplied for breathing purposes by the first pressurized gas supply. Further, the two separate pressurized gas supply sources for $P_1$ and $P_2$ can be provided by the same single gas pump and controlled by known control devices to be at the different desired pressures, or alternatively, two separate gas pumps can be used for the gas supplies to the mask interior 192 and the gusset chamber 190, respectively, to separately control each of $P_1$ and $P_2$.

Figure 24:
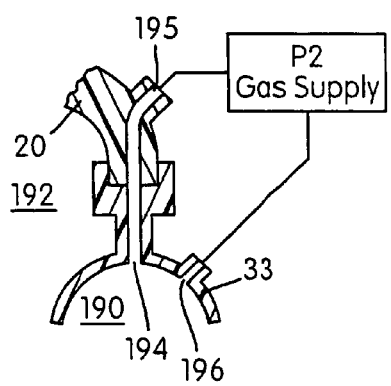
FIG. 24 shows a partial sectional view of another alternative of the embodiment of FIG. 21.

The gusset chamber 190 can be connected to the second gas supply through a port 194 in the gusset sidewall 33 connecting with a port 195 integrally molded with the mask shell 20 or can bypass the mask shell 20 and connect to the second gas supply through a port 196 in the gusset sidewall 33. See FIG. 24, which shows both alternatives.

The embodiment of FIG. 21 can have portions of the gusset sidewall 32 thickened/stiffened as discussed above with respect to FIGS. 12-14. However, the increased flexibility offered by controlling $P_2$ differently from $P_1$ means that the gusset sidewall can also be made generally uniform in thickness and a similar effect provided by the stiffening in the previously described embodiments can be provided in this embodiment merely by altering the pressure $P_2$ as desired.

Figure 22:
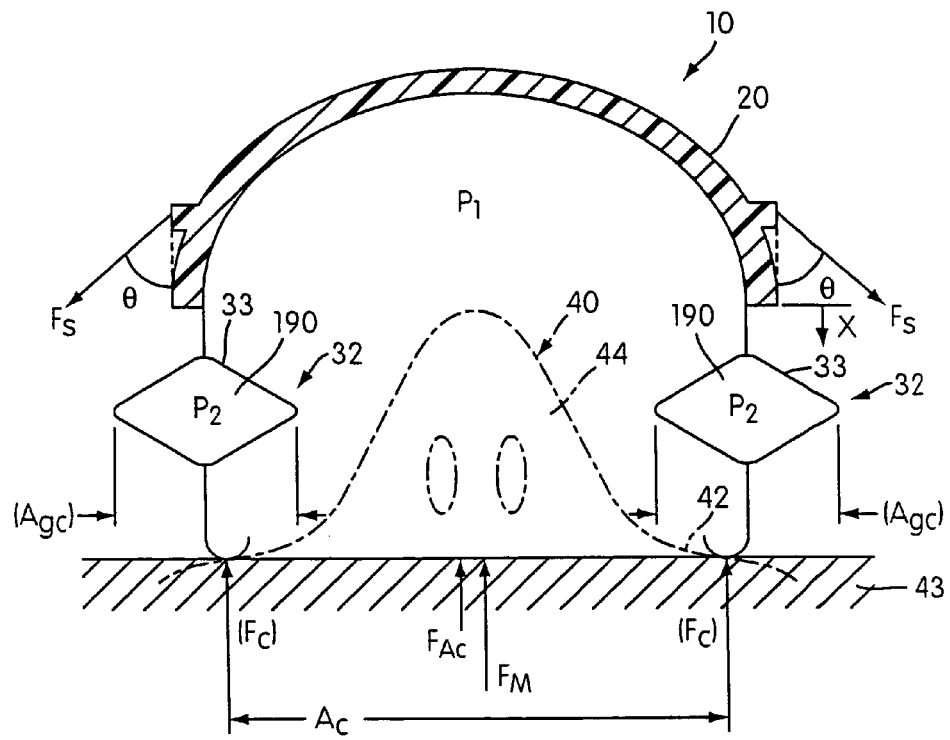
FIG. 22 shows a diagrammatic view of an alternative of the embodiment shown in FIG. 21.

In an alternative embodiment of the mask shown in FIG. 21, the gusset portion 32 can have a generally diamond-shaped cross-section when the mask 10 is not in use or not pressurized, as shown in FIG. 22, which cross-section can balloon to a generally circular cross-section when the gusset chamber is pressurized. Alternative shapes for the gusset portion 32 can also be used, including a piston/cylinder arrangement corresponding to FIG. 17 discussed above.

The cushion can also have alternative configurations. See FIGS. 25-30, which show partial sectional views of the cushion 30. In each of these embodiments, the cushion 30 is provided with a flexible membrane 170 that acts as a face-contacting portion 134. The flexible membrane 170 is attached to the more rigid supporting sidewall 173 of the cushion 30. These embodiments do not use an inner rim as does the embodiment shown in FIG. 9. In each embodiment, the face-contacting portion 134 extends beyond an axially outer end 174 of the sidewall 173 when the cushion is at rest. The face-contacting portion 134 can move axially with respect to the sidewall 173 to alter an axial distance between the face-contacting portion 134 and the axially outer end 174. That is, when a force is applied to the cushion toward the users' face, the face-contacting portion 134 will retract, axially moving toward the axially outer end 174 of the sidewall 173. The axially outer end 174 of the sidewall 173 will provide a generally positive end limit to this retraction when it contacts the user's face.

Figure 25:
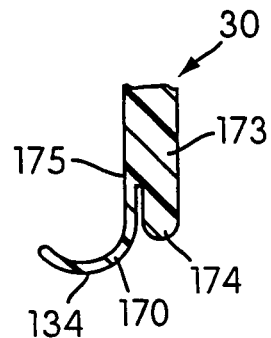
FIGS. 25-30 show partial sectional views of alternative embodiments of a mask cushion of the present invention.
Figure 26:
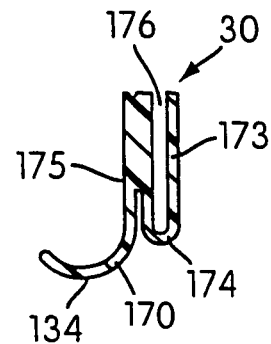

In the embodiments shown in FIGS. 25 and 26, the flexible membrane 170 is attached to the sidewall 173 at a position 175 axially inward from the axially outer edge 174, with a portion of the flexible membrane 170 extending axially outwardly alongside the sidewall 173 between the position 175 and the axially outer edge 174. In these embodiments, axial movement of the face-contacting portion 134 is substantially provided by the flexibility of the flexible membrane 170. If a less rigid sidewall 173 is desired, for instance, to be more comfortable to the user when the axially outer edge 174 contacts the user's face, the sidewall 173 can have a hollow portion 176, especially between the position 175 and the axially outer edge 174. See FIG. 26.

Figure 27:
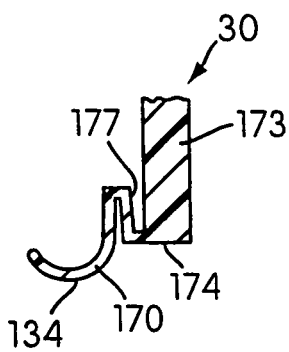
Figure 28:
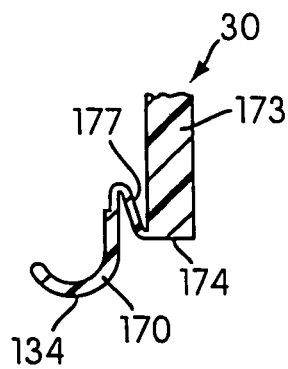
Figure 29:
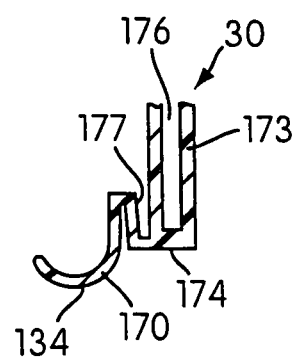
Figure 30:
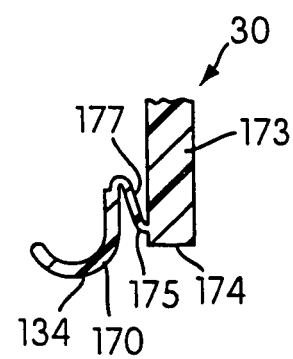

In the embodiments shown in FIGS. 27-30, the flexible membrane 170 is connected to the sidewall 173 by a flexible connecting member 177 that provides for axial movement between the flexible member 170 and the sidewall 173. The flexible connecting member 177 can have a generally straight cross-section, as seen in FIG. 27, a convoluted cross-section, as seen in FIG. 28, or another cross-section. The flexible connecting member 177 can be attached to the sidewall 173 near the axially outer end 174, as shown in FIGS. 27-29, or can be attached to the sidewall 173 at an axially inward position 175, as shown in FIG. 30. As with the embodiment of FIG. 26, the sidewall can be at least partially hollow to make the sidewall less rigid. See FIG. 29. In the preferred embodiment, the flexible membrane 170, the flexible connecting member 177 and the sidewall 173 are integrally molded together. Although the flexible membrane is shown as being attached to a cushion sidewall, it is contemplated that in alternative embodiments, the flexible membrane can be attached directly to the mask shell, with a portion of the mask shell acting as the axially outer edge 174.

The embodiments of FIG. 25-30 can be used in conjunction with the gusset-feature described above or can be used with known mask cushions. These embodiments provide good sealing characteristics with the face in a cushion that is easier and less expensive to manufacture than the known mask cushions. It is also to be understood that in the embodiments of FIGS. 27-30, the flexible connecting member can act similarly to the gusset feature described above when the mask is pressurized. That is, the pressure in the mask will act on the flexible connecting member 177 to impart an additional force on the face-contacting portion 134 of the flexible membrane 170 and that additional force will have the same characteristics as described above with respect to the above-described embodiments. In the embodiments of FIGS. 27-30, the area $A_c$ would be measured the same as in the embodiments above and the area $A_g$ would be measured to the interior surface of the sidewall 173 where the flexible connecting member 177 attaches to the sidewall 173.

Other alternative embodiments can use various combinations of any of the embodiments disclosed herein.

It should be recognized that the gusset portion of the present invention can be manufactured as a component separate from the cushion and mask shell but is attachable therebetween to provide the benefits described herein.

Figure 19:
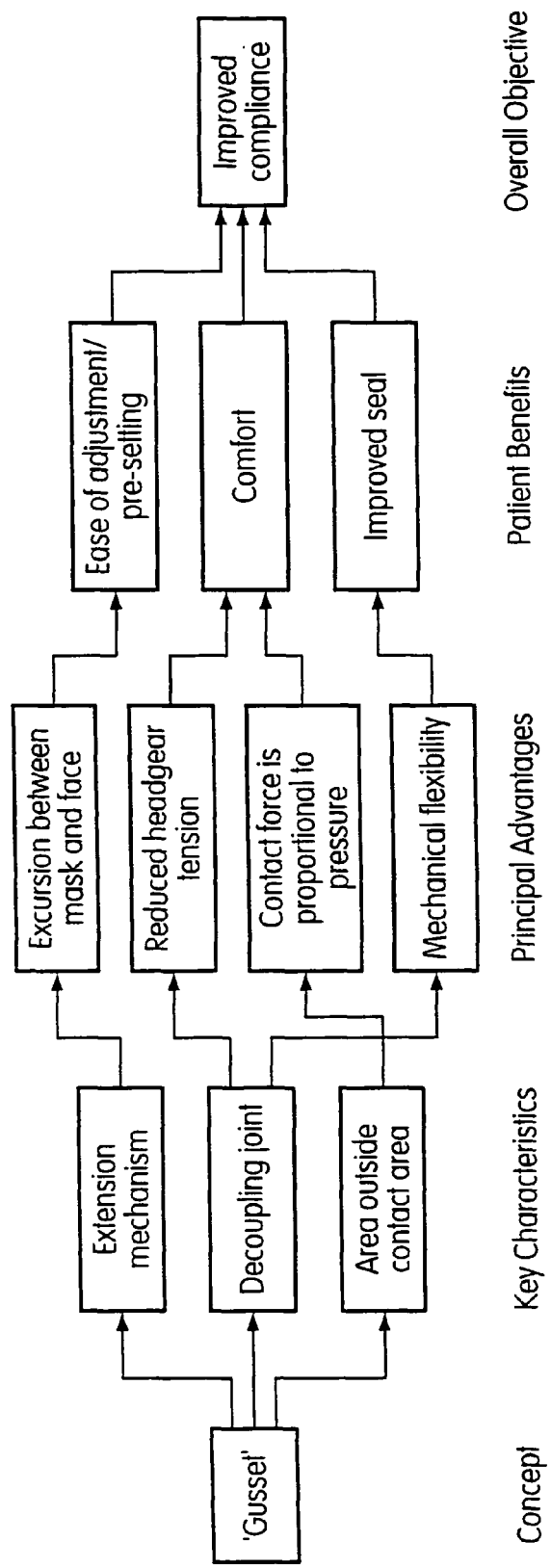
FIG. 19 diagrams the key characteristics, principal advantages and patient benefits deriving from the present invention and leading to increased therapy compliance by the patient.

The reduced contact force, total force on the face and headgear tension across the mask air pressure range and especially at mask air pressures below the maximum mask air pressure improves patient comfort, in particular for auto-titrating devices which start therapy at low pressures at the beginning of the night when the patient is trying to get to sleep. The improved seal (which can be obtained with a lower contact force) reduces sleep disturbance to patients and partners by substantially reducing the risk of leaks. The improved seal also increases the confidence of the patient in the seal, resulting in more comfortable therapy for the patient. See FIG. 19, which diagrams how the key characteristics of the gusset portion of the present invention mask provide principal advantages leading to patient benefits and improved compliance with a prescribed therapy.

Figure 20:
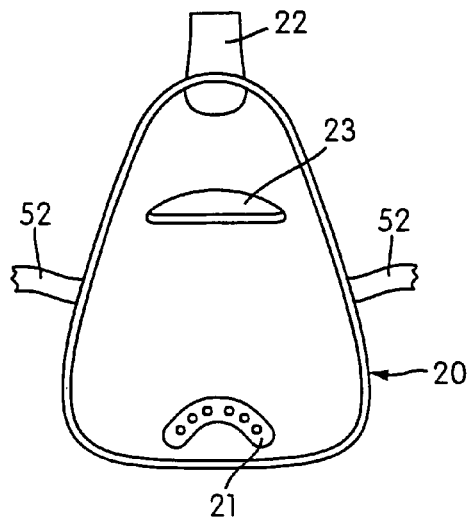
FIG. 20 shows an elevational view of the interior of the mask shell of one embodiment of the present invention.

Another aspect of the present invention is the inclusion of the baffle 23 in the mask shell 20. The employment of the baffle in the mask shell 20 improves the movement of air within the mask. In the embodiment shown in FIGS. 4, 5 and 20, the baffle 23 is in the form of a flat plate disposed between the mask intake 22 and the mask exhaust vent 21. The baffle 23 can extend into the mask generally horizontally or can tilt upward or downward. The baffle need not be in the form of a flat plate but can be V-shaped, curved, wavy or have some other configuration best designed to deflect air from the intake from directly flowing to the exhaust vent. The baffle 23 can be integrally molded with the mask shell or attached to the shell by other known methods, including adhesive or ultrasonic bonding. It should be understood that the mask shell incorporating the baffle can be used in combination with the gusset portion, but that either of these aspects can be used alone in a mask of the present invention.

While the invention has been described in accordance with what is presently believed to be the most practical and preferred embodiments, it is to be understood that the invention is not to be limited to the disclosed embodiments but on the contrary, is intended to cover various modifications and equivalent arrangements included within the spirit and the scope of the appended claims, which claims are to be interpreted in the broadest manner so as to encompass all such equivalent structures.

What is claimed is:

1. A breathable gas mask arrangement for sealed delivery of a flow of pressurized breathable gas at a continuously positive pressure with respect to ambient air pressure to a patient's airways, wherein the breathable gas mask arrangement is configured to maintain a therapy pressure in a range of about 4cmH$_2$O to about 25cmH$_2$O above ambient pressure in use, throughout the patient's respiratory cycle, while the patient is sleeping, to ameliorate sleep disordered breathing, said breathable gas mask arrangement comprising:

a mask shell having a portion adapted to receive a supply of said pressurized breathable gas and a patient side;

a gusset portion having a first side attached to the patient side of the shell and having a second side;

a cushion having a first portion attached to the second side of the gusset portion and a second portion constructed and arranged to contact a patient's face in use and provide a seal between the mask arrangement and the patient's face for delivery of said pressurized gas to the patient's airways; and wherein:

a distance between the mask shell and the cushion is variable, and the gusset portion defines a projected area having an outer extent determinative of contact force applied to the patient's face, said projected area is variable to vary the contact force in use dependent on the distance between the mask shell and the cushion, and a maximum width of the gusset portion over an operating pressure range is greater that a width of the mask shell at the patient side of the mask shell.

2. A breathable gas mask arrangement as claimed in claim 1, wherein the projected area is variable in a radial direction according to a pressure of the supplied breathable gas over an operating pressure range.

3. A breathable gas mask arrangement as claimed in claim 1, wherein the gusset portion comprises an elastic spring constant that varies according to (1) a pressure of the supplied breathable gas over an operating pressure range and/or (2) the distance between the shell and the cushion.

4. A breathable gas mask arrangement as claimed in claim 1, wherein the cushion is directly attached to an elastic sidewall of the gusset portion.

5. A breathable gas mask arrangement as claimed in claim 1, wherein an elastic sidewall of the gusset portion extends radially outward from the cushion.

6. A breathable gas mask arrangement as claimed in claim 1, further comprising headgear constructed to support the shell to the patient, said headgear including at least one strap.

7. A breathable gas mask arrangement as claimed in claim 6, wherein a component of contact force ($F_c$) provided by the supply of pressurized breathable gas acting on the projected area is sufficient to maintain the seal between the mask arrangement and the patient's face without adjusting strap tension.

8. A breathable gas mask arrangement as claimed in claim 7, wherein the strap tension upon initial set up of the mask arrangement does not exceed a value sufficient to bring the cushion in contact with the patient's face.

9. A breathable gas mask arrangement as claimed in claim 1, wherein the gusset portion consists of a single gusset.

10. A breathable gas mask arrangement as claimed in claim 1, wherein the projected area provided by the gusset portion on the patient's face is greater than an area of contact of the cushion with the patient's face.

11. A breathable gas mask arrangement as claimed in claim 1, wherein the projected area is a projected area on the patient's face of an interior of the gusset portion exposed to pressure.

12. A breathable gas mask arrangement as claimed in claim 1, wherein the projected area corresponds to a width between outer extents of the gusset portion across the cushion.

13. A breathable gas mask arrangement for sealed delivery of a flow of pressurized breathable gas at a continuously positive pressure with respect to ambient air pressure to a patient's airways, wherein the breathable gas mask arrangement is configured to maintain a therapy pressure in a range of about 4cmH$_2$O to about 25cmH$_2$O above ambient pressure in use, throughout the patient's respiratory cycle, while the patient is sleeping, to ameliorate sleep disordered breathing, said breathable gas mask arrangement comprising:

a mask shell having a portion adapted to receive a supply of said pressurized breathable gas and a patient side; and a cushion having a shell attachment portion attached to the patient side of the shell, a face contacting portion constructed and arranged to contact a patient's face in use and provide a seal between the mask arrangement and the patient's face for delivery of said pressurized gas to the patient's airways, and a gusset portion between the shell contacting portion and the face contacting portion, wherein a maximum width of the gusset portion over an operating pressure range is greater than a width of the mask shell at the patient side of the mask shell.

14. A breathable gas mask arrangement as claimed in claim 13, further comprising headgear including a plurality of straps to secure the mask arrangement to the patient, the straps arranged so they do not obstruct the patient's view in use.

15. A breathable gas mask arrangement as claimed in claim 14, further comprising a forehead support adapted to engage the patient's forehead in use, wherein upper straps of the headgear engage the forehead support and lower straps of the headgear engage the shell.

16. A breathable gas mask arrangement as claimed in claim 13, wherein the gusset portion includes only a single gusset having first and second side walls that define an angle therebetween, the first side wall formed as a continuous extension with the shell attachment portion and the second side wall formed as a continuous extension with the face contacting portion.

17. A breathable gas mask arrangement as claimed in claim 13, wherein the maximum width of the gusset portion over an operating pressure range is greater than the width of the mask shell where the cushion connects to the mask shell.

18. A breathable gas mask arrangement as claimed in claim 13, wherein the gusset portion defines a projected area having an outer extent determinative of contact force applied to the patient's face, said projected area is variable to vary the contact force in use dependent on a distance between the mask shell and the cushion.

19. A breathable gas mask arrangement as claimed in claim 13, wherein the gusset portion is adapted to define a projected area on the patient's face that is greater than an area of contact of the cushion with the patient's face.

20. A breathable gas mask arrangement for sealed delivery of a flow of pressurized breathable gas at a continuously positive pressure with respect to ambient air pressure to a patient's airways, wherein the breathable gas mask arrangement is configured to maintain a therapy pressure in a range of about 4cmH$_2$O to about 25cmH$_2$O above ambient pressure in use, throughout the patient's respiratory cycle, while the patient is sleeping, to ameliorate sleep disordered breathing, said breathable gas mask arrangement comprising:

a mask shell having a portion adapted to receive a supply of said pressurized breathable gas and a patient side; and a full-face cushion having a shell attachment portion attached to the patient side of the shell, a face contacting portion constructed and arranged to contact a patient's face in use and provide a seal between the mask arrangement and the patient's face for delivery of said pressurized gas to the patient's airways, and a gusset portion between the shell contacting portion and the face contacting portion, wherein:

the face contacting portion includes a flexible membrane distinct from walls of the gusset portion, and a maximum width of the gusset portion over an operating pressure range is greater than a width of the mask shell at the patient side of the mask shell.

21. The breathable gas mask arrangement as claimed in claim 20, wherein the cushion is adapted to provide a seal around the patient's nose and mouth.

22. The breathable gas mask arrangement as claimed in claim 20, wherein the cushion is integrally molded of a silicone material.

23. The breathable gas mask arrangement as claimed in claim 20, further comprising headgear constructed and arranged to support the mask shell to the patient, wherein the headgear includes upper side straps adapted to pass over the patient's ears and lower side straps adapted to pass below the patient's ears.

24. The breathable gas mask arrangement as claimed in claim 20, wherein side walls of the gusset portion have a generally uniform thickness.

25. The breathable gas mask arrangement as claimed in claim 20, wherein the gusset portion is constructed and arranged such that it can expand and contract to alter a distance between the mask shell and the cushion.

26. The breathable gas mask arrangement as claimed in claim 25, wherein the distance is within a range of movement of the gusset portion that is greater than 0 mm and less than 30 mm.

27. A breathable gas mask arrangement as claimed in claim 20, wherein the flexible membrane is adapted to provide a seal around the patient's nose and mouth.

28. A breathable gas mask arrangement for sealed delivery of a flow of pressurized breathable gas at a continuously positive pressure with respect to ambient air pressure to a patient's airways, wherein the breathable gas mask arrangement is configured to maintain a therapy pressure in a range of about 4cmH$_2$O to about 25cmH$_2$O above ambient pressure in use, throughout the patient's respiratory cycle, while the patient is sleeping, to ameliorate sleep disordered breathing, said breathable gas mask arrangement comprising:
- a mask shell having a portion adapted to receive a supply of said pressurized breathable gas and a patient side;
- a gusset portion having a first side attached to the patient side of the shell and having a second side;
- a cushion having a first portion attached to the second side of the gusset portion and a second portion constructed and arranged to contact a patient's face in use and provide a seal between the mask arrangement and the patient's face for delivery of said pressurized gas to the patient's airways; and
- headgear constructed and arranged to attach the mask shell to the patient;
- wherein the gusset portion includes an elastic sidewall having a spring constant that is at least partially determinative of a force applied to the patient's face through the second portion of the cushion, and
- a maximum width of the gusset portion over an operating pressure range is greater than a width of the mask shell at the patient side of the mask shell.

29. The breathable gas mask arrangement as claimed in claim 28, wherein the gusset portion is constructed and arranged such that it can expand and contract to alter a distance between the mask shell and the cushion.

30. The breathable gas mask arrangement as claimed in claim 29, wherein the distance is within a range of movement of the gusset portion that is greater than 0 mm and less than 30 mm.

31. The breathable gas mask arrangement as claimed in claim 28, wherein an interior of the gusset portion is exposed to the supply of pressurized breathable gas and adapted to provide a projected area on the patient's face ($A_g$) which is greater than an area ($A_c$) of contact of the cushion with the patient's face.

32. The breathable gas mask arrangement as claimed in claim 28, wherein the gusset portion includes a single gusset having a flexible sidewall.

33. The breathable gas mask arrangement as claimed in claim 28, wherein the cushion and gusset are molded of a silicone material.

34. The breathable gas mask arrangement as claimed in claim 28, wherein the second portion of the cushion includes a flexible membrane and an inner rim that provides a backing element for the membrane.

35. The breathable gas mask arrangement as claimed in claim 34, wherein the membrane and the inner rim are connected to a relatively rigid side wall that attaches to the gusset portion.

36. The breathable gas mask arrangement as claimed in claim 28, wherein the headgear includes upper side straps adapted to pass over the patient's ears and lower side straps adapted to pass below the patient's ears.

37. The breathable gas mask arrangement as claimed in claim 28, wherein the side wall includes a thickened base.

38. The breathable gas mask arrangement as claimed in claim 28, wherein the cushion and gusset portion meet at an intersection.

39. The breathable gas mask arrangement as claimed in claim 38, wherein the cushion and gusset portion form a substantially continuous surface.

40. The breathable gas mask arrangement as claimed in claim 38, wherein the cushion and gusset portion are angled with respect to one another.

41. The breathable gas mask arrangement as claimed in claim 28, wherein the gusset portion is adapted to define a projected area on the patient's face that provides a component of a contact force of the cushion on the patient's face.

42. The breathable gas mask arrangement as claimed in claim 41, wherein the mask arrangement is adapted to define a ratio of the projected area of the gusset portion on the patient's face to an area of contact of the cushion with the patient's face of at least 1.30.

43. The breathable gas mask arrangement as claimed in claim 28, wherein the gusset portion extends radially outwardly from the cushion around the entire perimeter of the cushion.

* * * * *

UNITED STATES PATENT AND TRADEMARK OFFICE
CERTIFICATE OF CORRECTION

PATENT NO.        : 8,978,653 B2                                               Page 1 of 1
APPLICATION NO.   : 11/430051
DATED             : March 17, 2015
INVENTOR(S)       : Frater et al.

It is certified that error appears in the above-identified patent and that said Letters Patent is hereby corrected as shown below:

In the claims:

In claim 1, at column 15, line 13, "pressure range is greater that a width of the mask shell at" should be corrected to ---pressure range is greater than a width of the mask shell at---.

Signed and Sealed this
Eighteenth Day of August, 2015

Michelle K. Lee
*Director of the United States Patent and Trademark Office*